(12) United States Patent
Koo et al.

(10) Patent No.: US 6,268,155 B1
(45) Date of Patent: Jul. 31, 2001

(54) METHOD FOR QUANTITATING AN INFLAMMATORY RESPONSE

(75) Inventors: Gloria C. Koo, Woodbridge; Mai P. Nguyen, Tinton Falls; Althea D. Talento, Convent Station, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/711,768

(22) Filed: Sep. 10, 1996

Related U.S. Application Data

(60) Provisional application No. 60/003,990, filed on Sep. 19, 1995.

(51) Int. Cl.⁷ .......................... G01N 33/53; G01N 33/567
(52) U.S. Cl. ...................... 435/7.1; 435/7.2; 435/7.21; 435/7.24; 435/7.92; 435/7.94
(58) Field of Search .................................... 435/792, 723

(56) References Cited

U.S. PATENT DOCUMENTS 5,202,230  4/1993  Kamentsky ............... 435/6
5,426,029  6/1995  Rittershaus et al. .

OTHER PUBLICATIONS

Di Carlo, et al., *J. Neurosurg. Sci.*, vol. 34, No. 3–4, p. 181–5, Jul.–Dec. 1990. Abstract only.*

Kang, K. et al., "CD11b+ Macrophages That Infiltrate Human Epidermis After In Vivo Ultraviolet Exposure Potently Produce IL–10 and Represent the Major Secretory Source of Epidermal IL–10 Protein1", J. Immunol., vol. 153, pp. 5256–5264, 1994.

* cited by examiner

*Primary Examiner*—Anthony C. Caputa
(74) *Attorney, Agent, or Firm*—Valerie J. Camara; Mark R. Daniel

(57) ABSTRACT

A method for objectively quantitating the cellular infiltration in a tissue biopsy of a warm-blooded animal using a capture ELISA method. This method also allows one to quantitate the cellular infiltration of a tissue biopsy corresponding to an inflammatory response. As such this invention has both research and clinical applications in the analysis of an inflammatory response, and the effectiveness of immunosuppresants in addressing the inflammation.

10 Claims, 1 Drawing Sheet

METHOD FOR QUANTITATING AN INFLAMMATORY RESPONSE

This application claims benefit of provisional application Ser. No. 60/003,990, filed Sep. 19, 1995.

BACKGROUND OF THE INVENTION

The assessment of inflammatory responses has been achieved by subjective analysis either by actual measurement and scoring or through the use of immunohistochemistry of the inflammatory response. Among the types of inflammatory responses is delayed type hypersensitivity response (DTH), which results in redness and swelling, due to exposure to a sensitizing antigen, similar to an allergic reaction.

In order to objectively quantify cellular infiltration in a skin DTH response a novel methodology was developed. The procedure involves a new method for solubilizing a skin biopsy and then quantifying the surface antigen expressed by the infiltrating leukocytes in the solubilized skin biopsy. This quantification is made possible by applying a capture ELISA (enzyme linked i mnmunoadsorbant assay) using two monoclonal antibodies. This methodology will allow for the quantification of DTH responses, as well as any cellular antigens in tissues and biopsies, provided there are two monoclonal or polyclonal antibodies available to detect the antigen. An objective method for quantifying an inflammatory response to date has not been developed.

SUMMARY OF THE INVENTION

The instant invention relates to a method for quantitating a cellular infiltrate in a tissue biopsy of a warm-blooded animal comprising the steps of: (a) solubilizing the tissue biopsy to isolate a tissue antigen in the supernatant; and (b) measuring the surface antigen expressed by the cellular infiltration found in the tissue supernatant isolated from the tissue biopsy of the inflammatory response, using a capture ELISA method. This method also allows one to quantitate the cellular infiltration of a tissue biopsy corresponding to an inflammatory response. As such this invention has both research and clinical applications in the analysis of an inflammatory response, and the effectiveness of immunosuppressants in addressing the inflammation.

DETAILED DESCRIPTION OF THE INVENTION

Figure 1:
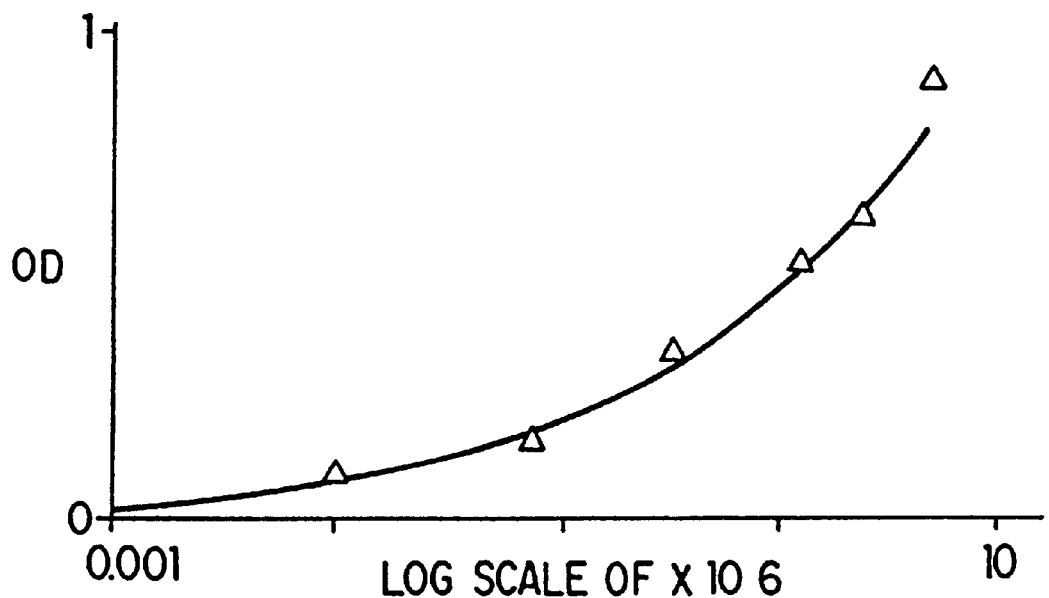
FIG. 1 Standard curve for CD2 cell surface antigen plotted by measuring the optical density of MNC lysate samples at 1:4, 1:8, 1:16, 1:64, 1:256, and 1:1024 dilutions, with cell number/ml on the X-axis and optical density (O.D.) on the Y-axis. [Curve fit is 4-parameter: $y+(A-D)/(1+x/C)^B)+D$ {A=−0.0294, B=0.338, C=7.62E+03, D=10.8} Correlation Coefficient=0.991]

The instant invention relates to a method for quantitating a cellular infiltrate in a tissue biopsy of a warm-blooded animal comprising the steps of:

(a) solubilizing the tissue biopsy to isolate a tissue supernatant; and (b) quantitating the extent of cellular infiltration of the tissue supernatant by measuring the surface antigen expressed by the cellular infiltration found in the tissue supernatant isolated from the tissue biopsy of the inflammatory response, using a capture ELISA method.

A first embodiment of this invention is the method for quantitating an inflammatory response in a tissue biopsy of a warm-blooded animal comprising the steps of:

(a) solubilizing the tissue biopsy to isolate a tissue supernatant; and (b) quantitating the flammatory response of the tissue supernatant by measuring the surface antigen expressed by the infiltrating leukocytes found in the tissue supernatant isolated from the tissue biopsy of the inflammatory response, using a capture ELISA method.

An second embodiment of this invention is the method for quantitating an inflammatory response in a tissue biopsy of a warm-blooded animal comprising the steps of:

(a) mincing the tissue biopsy in an ice cold lysing buffer to produce a minced tissue biopsy suspension;

(b) cooling on ice the minced tissue biopsy suspension for 30 minutes;

(c) spinning the cooled, minced tissue biopsy suspension;

(d) decanting a tissue supernatant from the spun tissue biopsy suspension; and (e) quantitating the inflammatory response of the tissue supernatant by measuring the surface antigen expressed by the infiltrating cells found in the tissue supernatant isolated from the tissue biopsy of the inflammatory response, using a capture ELISA method A sub-embodiment of second embodiment of this invention is the method as recited above wherein the capture ELISA method comprises:

(a) reacting the tissue supernatant with a first antibody, Ab(A) for a period of 12 to 16 hours;

(b) washing the reaction mixture with 0.05% Tween in PBS solution;

(c) reacting the Ab(A)-linked tissue supernatant with a second antibody which is conjugated with biotin, Ab(B);

(d) washing the reaction mixture with 0.05% Tween in PBS solution;

(e) reacting the Ab(B)-Ab(A)-linked tissue supernatant with a avidin-peroxidase;

(f) washing the reaction mixture with 0.05% Tween in PBS solution;

(g) reacting with substrate, o-phenylenediamine dihydrochloride;

(h) measuring the optical density of the reaction of avidin-peroxidase-Ab(B)-Ab(A)-linked tissue supernatant with the substrate; and (i) calculating a cellular concentration from the optical density measured using a standard curve.

A third embodiment of this invention is the method for quantitating an inflammatory response in a tissue biopsy of a mini-pig comprising the steps of:

(a) mincing the tissue biopsy of the mini-pig in an ice cold lysing buffer to produce a minced tissue biopsy suspension;

(b) cooling on ice the minced tissue biopsy suspension for 30 minutes;

(c) spinning the cooled, minced tissue biopsy suspension;

(d) decanting a tissue supernatant from the spun tissue biopsy suspension; and (e) quantitating the inflammatory response of the tissue supernatant by measuring the surface antigen expressed by the infiltrating cells found in the tissue supernatant isolated from the tissue biopsy of the inflammatory response, using a capture ELISA method A sub-embodiment of third embodiment of this invention is the method as recited above wherein the capture ELISA method comprises:

(a) reacting the tissue supernatant with a first antibody, Ab(A) for a period of 12 to 16 hours;

(b) washing the reaction mixture with 0.05% Tween in PBS solution;

(c) reacting the Ab(A)-linked tissue supernatant with a second antibody which is conjugated with biotin, Ab(B);

(d) washing the reaction mixture with 0.05% Tween in PBS solution;

(e) reacting the Ab(B)-Ab(A)-linked tissue supernatant with a avidin-peroxidase;

(f) washing the reaction mixture with 0.05% Tween in PBS solution;

(g) reacting with substrate, o-phenylenediamine dihydrochloride;

(h) measuring the optical density of the reaction of avidin-peroxidase-Ab(B)-Ab(A)-linked tissue supernatant with the substrate; and (i) calculating a cellular concentration from the optical density measured using a standard curve.

A fourth embodiment of this invention is the method for quantitating a DTH inflammatory response in a tissue biopsy of a mini- pig comprising the steps of:

(a) removing a tissue biopsy of the DTH inflammatory response from the mini-pig;

(b) mincing the tissue -biopsy in an ice cold lysing buffer to produce a minced tissue biopsy suspension;

(c) cooling on ice the minced tissue biopsy suspension for 30 minutes;

(d) spinning the cooled, minced tissue biopsy suspension;

(e) decanting a tissue supernatant from the spun tissue biopsy suspension;

(f) quantitating the DTH inflammatory response of the tissue supernatant by measuring the surface antigen expressed by the infiltrating cells found in the tissue supernatant isolated from the tissue biopsy of the inflammatory response, using a capture ELISA method.

A sub-embodiment of fourth embodiment of this invention is the method as recited above wherein the capture ELISA method comprises:

(a) reacting the tissue supernatant with a first antibody, Ab(A) for a period of 12 to 16 hours;

(b) washing the reaction mixture with 0.05% Tween in PBS solution;

(c) reacting the Ab(A)-linked tissue supernatant with a second antibody which is conjugated with biotin, Ab(B);

(d) washing the reaction mixture with 0.05% Tween in PBS solution;

(e) reacting the Ab(B)-Ab(A)-linked tissue supernatant with a avidin-peroxidase;

(f) washing the reaction mixture with 0.05% Tween in PBS solution;

(g) reacting with substrate, o-phenylenediamine dihydrochloride;

(h) measuring the optical density of the reaction of avidin-peroxidase-Ab(B)-Ab(A)-linked tissue supernatant with the substrate; and (i) calculating a cellular concentration from the optical density measured using a standard curve.

A fifth embodiment of this invention is the method as recited above wherein the capture ELISA method comprises:

(a) incubating a 96-well plate treated with a first antibody Ab(A) for a period of 18 to 24 hours;

(b) washing the first antibody Ab(A) treated 96-well plate to remove the excess antibody Ab(A);

(c) blocking the plate with 3% bovine serum albumin in a phosphate buffer;

(d) reacting the tissue supernatant with the first antibody Ab(A) coated 96-well plate for a period of 12 to 16 hours;

(e) washing the reaction mixture with 0.05% Tween in PBS solution;

(f) reacting the washed 96-well plate containing the Ab(A)-linked tissue supernatant with a second antibody which is conjugated with biotin Ab(B);

(g) washing the 96-well plate containing the Ab(B)-Ab(A)-linked tissue supernatant with 0.05% Tween in PBS solution;

(h) reacting the washed 96-well plate containing the Ab(B)-Ab(A)-linked tissue supernatant with a avidin-peroxidase;

(i) washing the avidin-peroxidase treated 96-well plate containing the Ab(B)-Ab(A)-linked tissue supernatant with 0.05% Tween in PBS solution;

(j) reacting the washed avidin-peroxidase treated 96-well plate containing the Ab(B)-Ab(A)-linked tissue supernatant with substrate, o-phenylenediamine dihydrochloride;

(k) measuring optical density of the substrate-avidin-peroxidase- Ab(B)-Ab(A)-linked tissue supernatant; and (l) calculating a cellular concentration from the optical density measured using a standard curve.

A sixth embodiment of this invention is the method for quantitating the pharmaceutical effectiveness of a test compound to inhibit or reduce the amount of cellular infiltration in a inflammatory response of a mammal comprising the steps of:

(a) solubilizing a control tissue biopsy from mammal to isolate a tissue supernatant;

(b) measuring optical density of a surface antigen expressed by the cellular infiltration found in the tissue supernatant isolated from the control tissue biopsy, using a capture ELISA method;

(c) treating the mammal with a test compound at a dose of about 8 $\mu$g/kg –30 mg/kg;

(d) solubilizing a test tissue biopsy after treatment with the test compound to isolate a tissue supernatant;

(e) quantitating the inflammatory response to the tissue supernatant by measuring optical density of a surface antigen expressed by the cellular infiltration found in the tissue supernatant isolated from the test tissue biopsy, using a capture ELISA method;

(f) calculating a cellular concentration from the measured optical density of the control and the test tissue biopsies using a standard curve;

(g) comparing the cellular infiltration concentration of the test tissue biopsy to the control tissue biopsy.

The instant invention provides a methodology useful in quantitating the effectiveness of an immunosuppressant test compound, for example an ion channel blocker (Kv1.3 blocker), in reducing the cellular infiltration and thus the inflammatory response. The instant invention provides a method for objectively quantitating the effectiveness of test compounds.

The effectiveness of immunosuppressant test compounds can be evaluated by creating a DTH inflammatory response in a laboratory animal, such as a mini-pig, and subsequently treating the test animals with the immunosuppressant compound, then following the methodology of the instant invention to quantitate the effectiveness.

A tissue biopsy in the instant invention refers to a tissue sample which contains a cellular infiltrate of interest and to which antibodies to the cellular infiltrate are available.

A cellular infiltrate includes: leukocytes, lymphocytes, and monocytes.

For the purpose of this disclosure, animal is a member of the animal kingdom which includes but is not limited to mammals and birds. The selected mammals of this invention are mini-pigs for research purposes and humans for clinical evaluation.

A solubilization (lysing) buffer comprises 10 mM pH 8.0 Tris[hydroxymethyl]aminomethane hydrochloride(Tris-HCl), 0.15 M NaCl, 0.15 % TritonX-100, 1 mM ethylene-diaminetetraacetic acid (EDTA), 30 $\mu$M isovaleryl-Val-Val Sta-Ala-Sta (Pepstatin A), 1 mM (tetrathionate), and 1 mM phenyl methylsulfonyl fluoride (PMSF), all of which are available from Sigma Chemical Company, St. Louis, Mo., hereinafter referred to as Sigma.

The tissue sample is minced or polytroned (Polytron, Brink man Instrument. Westbury, N.Y.) to small pieces in the cold solubilization (lysing) buffer.

The carbonate buffer comprises of 0.75 g/500 ml sodium carbonate and 1.465 g/500 ml sodium bicarbonate. The carbonate buffer solution is then adjusted to a pH of 9.6 with sodium hydroxide.

The citric-phosphate buffer consists of 0.1 M $Na_2HPO_4$ (14.42 g/l), 0.1M citric acid (19.2 g/liter). The citric-phosphate buffer solution is then adjusted to a pH 5.0 with phosphoric acid.

A 3% bovine serum albumin in phosphate buffered saline (PBS) solution [PBS comprises of sodium chloride, potassium chloride and phosphate buffer salts (GIBCO)].

0.05% Tween 20 (polyoxyethylenesorbitan monolaurate, Sigma) in PBS solution referred to as PBS-T buffer.

A capture ELISA method comprises the use of two (monoclonal or polyclonal) antibodies to the same antigen with two different epitopes, one of which is conjugated with biotin. The antigen containing supernatant is reacted with the first antibody and washed with a buffer solution. The antibody linked antigen is then reacted with the second antibody which is conjugated with biotin-N-hydroxy succinamide (biotin, Zymed) and then washed to remove the excess antibody. The antibody-biotin-antibody linked antigen is then cross-linked with avidin-peroxidase and washed to remove the excess antibody. Finally, a substrate is reacted with the avidin-peroxidase-crosslinked-antibody-biotin(B)-antibody(A) linked antigen, the color product of which upon development is measured by O.D. with an ELISA reader.

The ELISA analysis of pig cell surface antigens such as CD2, CD11 or CD18 were performed using the appropriate antibodies: anti-CD2, anti-CD11 and anti-CD18, which are available from VMRD Inc., Pullman, Wash. Samples of monoclonal anti-CD2 (MSA-4) was purchased from Dr. David Sachs at Massachusetts General Hospital, Boston, Mass. Antibodies to human cell surface antigens are available from Becton-Dickinson, San Jose, Calif. and Serotec Co., Oxford, UK, among others. Also, antibodies to mouse cell surface antigens are available from Pharmingen, San Diego, Calif. or Becton Dickinson among others.

Horse-radish-peroxidase conjugated with streptavidin available from Zymed, San Francisco, Calif., as well as Cappel Co. Melvern, Pa., among others.

Substrate is o-phenylenediamine dihydrochloride (OPD) in tablet form also available from Sigma Chemical Company.

The developing reagent, namely the streptavidin-peroxidase could be substituted by any streptavidin or avidin-linked indicator system, for example, alkaline phosphatase, Europium, or chemiluminescence and its respective developing substrate or indicator, generically referred to as substrate.

The process of this invention can be understood further by the following examples, which do not constitute a limitation of the invention.

EXAMPLE 1

Step A: Preparation of Yucatan pig tissue biopsy

The Yucatan pig skin biopsies are rinsed in phosphate buffered saline [(PBS) Dulbecco, GIBCO)], and trimmed of fatty tissue. The pig biopsies are then POLYTRONED or minced in 3 ml of TritonX-100 lysing buffer. The polytron probe is rinsed with 1 ml of TritonX-100 lysing buffer bringing the total volume of lysate to 4 ml. After incubation on ice (4° C.) for 20–30 minutes each lysate is divided into 3 eppendorf tubes and centrifuged in the cold for 20 minutes at 12,000 rpm. Supernatants from the tubes are combined and mixed thoroughly and aliquoted into 3 or 4 sets and stored at −70° C. until time of assay. The pig skin biopsy lysate samples can also be tested immediately. The pig skin biopsy lysate samples are tested neat or are diluted with TritonX-100 lysing buffer (includes protease inhibitors) in a 1:2 and 1:4 dilution of lysate sample in TritonX-100 lysis buffer.

Step B: Preparation of pig mononuclear cells (MNC) lysate for standard in the ELISA The pig mononuclear cells are purified from heparinized whole pig blood by ficoll-hypaque separation (lymphocyte separation media (LSM), Organon Teknika Co., Durham, N.C.). These cells are washed three times in cold PBS (GIBCO). The cells are then counted and lysed with TritonX-100 lysing buffer at a concentration of $20 \times 10^6$ cells per ml at 4° C. for 30 minutes. The lysates are spun at 800–1000 rpm to remove nuclei. The lysates are stored frozen at −70° C. All new lysate preparations are tested in DTH ELISA and compared to current standard. (A 1:4 dilution of Yucatan pig lysate in TritonX-100 lysing buffer is equal to $5 \times 10^6$ cell equivalents and should give an optical density value of 1.200–1.500@ 490nm.) The pig MNC lysate samples are diluted with TritonX-100 lysis buffer (includes protease inhibitors) in a 1:4, 1:8, 1:16, 1:64, 1:256, and 1:1024 dilution of MNC lysate sample in TritonX-100 lysis buffer for use as standards in the capture ELISA.

Step C: Method for quantitating the cellular infiltration of the tissue biopsy using a capture ELISA method.

Figure 2:
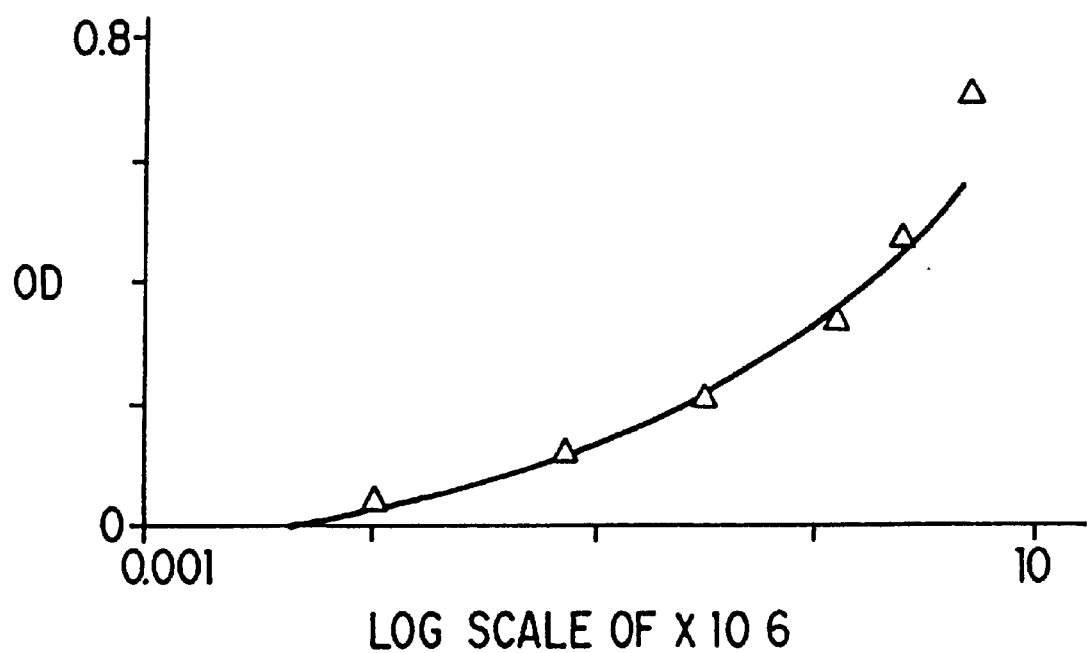
FIG. 2 Standard curve for CD18 cell surface antigen plotted by measuring the optical density of NMC lysate samples at 1:4, 1:8, 1:16, 1:64, 1:256, and 1:1024 dilutions, with cell number/ml on the X-axis and optical density (O.D.) on the Y-axis. [Curve fit is 4-parameter: $y+(A-D)/(1+x/C)^B) +D$ {A=−0.0862, B=0.280, C=1.09E+06, D-20.4} Correlation Coefficient=0.996]

A series of 96 well Maxisorp (Nunc, Denmark) plates are coated with an antibody A [a) Anti Pig CD2 (PG068-A) at 5 $\mu$g/ml or b) Anti Pig CD11a/CD18 (MUC76-A) at 0.7 $\mu$g/ml] diluted in carbonate buffer pH 9.6 for at least 18 hours. The plates are always kept at 4° C. or can be frozen at −20° C. The plates are then washed twice with 0.05% Tween 20 in PBS buffer (PBS-T) [PBS buffer is free of $Ca^{+2}$ and $Mg+^2$ ions]. The plates are blocked with 3% Bovine Serum Albumin in PBS buffer containing $Ca^{2+}$ & $Mg^{2+}$ ions [blocking buffer, BSA(RIA-grade, Sigma)] for 1 hr. @ 37° C. or overnight @ 4° C. The plates are then washed three times with PBS-T buffer. Aliquots of 100 $\mu$l of standard MNC and pig skin biopsy lysates are added to the blocked plates and incubated overnight at 4° C. The plates are then washed six times with PBS-T buffer. To the washed plates is added 100 μl of the biotinylated antibody [a) biotinylated Anti pig CD2 (MSA-4) at 1 μg/ml or b) biotinylated anti Human CD18 (IB-4) at 10 μg/ml. IB4 crossreacts with pig CD18]. The plates are incubated for 1 hour at 37° C. The plates are then washed six times with PBS-T buffer. A 100 μl aliquot of Streptavidin/HRP ( Zymed #43-4323)] diluted in blocking buffer [3% BSA in PBS (the blocking buffer should be free of azide) is added and incubated for 1 hour at 37° C. The plates are then washed six times with PBS-T buffer and then an aliquot of 100 g1 of the o-phenylenediamine dihydrochloride substrate solution was added. The o-phenylenediamine dihydrochloride substrate solution consists of 20 mg (2 tablets) o-phenylenediamine dihydrochloride in 25 ml of citrate-phosphate buffer of pH 5.0, 25 ml double distilled $H_2O$ and 18 μl of 30% $H_2O_2$. The substrate solution should be mixed well and stored out of the light. The color should develop in 5–10 minutes. The reaction is then stopped by the addition of 100 μl of 2N $H_2SO_4$. The plates are then each read at 490 nm. using an ELISA optical density reader (Molecular Device, Palo Alto, Calif.). Using a four-parameter curve fitting program, the standard curve is plotted by measuring the optical density of MNC lysate samples at 1:4, 1:8, 1:16, 1:64, 1:256, and 1:1024 dilutions, with cell number/ml on the X-axis, and optical density (O.D.) on the Y-axis (See FIGS. 1 and 2). The optical density of the plates containing the pig skin biopsy lysates is measured and the cell number/ml is read off this standard curve.

| Standard | Std Value ($10^6$) | OD | Mean O.D. | Std. Dev. | CV | Calc. Value ($10^6$) |
|---|---|---|---|---|---|---|
| STD01 | 5.000 | 0.789 1.015 | 0.902 | 0.160 | 17.72 | 4.686 10.31 |
| STD02 | 2.500 | 0.617 0.617 | 0.617 | ***** | ***** | 2.217 2.217 |
| STD03 | 1.250 | 0.525 0.520 | 0.522 | 0.004 | 0.677 | 1.371 1.333 |
| STD04 | 0.310 | 0.332 0.351 | 0.341 | 0.013 | 3.936 | 0.366 0.428 |
| STD05 | 0.070 | 0.180 0.144 | 0.162 | 0.025 | 15.73 | 0.070 0.040 |
| STD06 | 0.010 | 0.099 0.089 | 0.094 | 0.007 | 7.536 | 0.016 0.013 |
| BIOPSY | | 0.325 0.347 | 0.337 | 0.025 | 9.729 | 0.240 0.275 |
| STD01 | 5.000 | 0.632 0.776 | 0.704 | 0.102 | 14.47 | 7.614 15.03 |
| STD02 | 2.500 | 0.430 0.494 | 0.462 | 0.045 | 9.802 | 2.252 3.461 |
| STD03 | 1.250 | 0.301 0.365 | 0.333 | 0.045 | 13.60 | 0.786 1.375 |
| STD04 | 0.310 | 0.187 0.230 | 0.208 | 0.030 | 14.61 | 0.221 0.376 |
| STD05 | 0.070 | 0.089 0.145 | 0.117 | 0.040 | 33.94 | 0.044 0.121 |
| STD06 | 0.010 | 0.027 0.062 | 0.044 | 0.025 | 56.03 | 0.009 0.024 |
| BIOPSY | | 0.249 0.232 | 0.240 | 0.057 | 13.35 | 0.465 0.385 |

EXAMPLE 2

Following the procedure described above using pig tissue biopsies from a delayed type hypersensitivity (DTH) inflammatory response the cellular infiltration is measured.

EXAMPLE 3

General Procedure for Quantitating the Cellular Infiltration of a Biopsy

A similar procedure can be used to quantify cellular components or constituents in a biopsy, other than that in an inflammatory response, provided that there are two antibodies (polyclonal or monoclonal) available to detect different epitopes of the same antigen. Another criteria is that a standard curve of the cellular component could be generated, so that the quantification could be achieved.

What is claimed is:

1. A method for quantitating a cellular infiltration in a tissue biopsy of a warm-blooded animal comprising the steps of:
   (a) solubilizing the tissue biopsy to isolate a tissue supernatant; and
   (b) quantitating the extent of cellular infiltration of the tissue supernatant by measuring the surface antigen expressed by the cellular infiltration found in the tissue supernatant isolated from the tissue biopsy of the inflammatory response, using a capture ELISA method.

2. A method for quantitating an inflammatory response in a tissue biopsy of a warm-blooded animal comprising the steps of: (a) solubilizing the tissue biopsy to isolate a tissue supernatant; and
   (b) quantitating the inflammatory response of the tissue supernatant by measuring the surface antigen expressed by the infiltrating leukocytes found in the tissue supernatant isolated from the tissue biopsy of the inflammatory response, using a capture ELISA method.

3. A method for quantitating an inflammatory response in a tissue biopsy of a warm-blooded animal comprising the steps of:
   (a) mincing the tissue biopsy in an ice cold lysing buffer to produce a minced tissue biopsy suspension;
   (b) cooling on ice the minced tissue biopsy suspension for about 30 minutes;
   (c) spinning the cooled, minced tissue-biopsy suspension;
   (d) decanting a tissue supernatant from the spun tissue biopsy suspension; and
   (e) quantitating the inflammatory response of the tissue supernatant by measuring the surface antigen expressed by the infiltrating cells found in the tissue supernatant isolated from the tissue biopsy of the inflammatory response. using a capture ELISA method.

4. The method for quantitating an inflammatory response in a tissue biopsy of a mini-pig, as recited in claim 3, comprising the steps of:
   (a) mincing the tissue biopsy of the mini-pig in an ice cold lysing buffer to produce a minced tissue biopsy suspension;
   (b) cooling on ice the minced tissue biopsy suspension for about 30 minutes;
   (c) spinning the cooled, minced tissue biopsy suspension;
   (d) decanting a tissue supernatant from the spun tissue biopsy suspension; and
   (e) quantitating the inflammatory response of the tissue supernatant by measuring the surface antigen expressed by the infiltrating cells found in the tissue supernatant isolated from the tissue biopsy of the inflammatory response, using a capture ELISA method.

5. A method for quantitating a DTH inflammatory response of a mini-pig comprising the steps of:
   (a) removing a tissue biopsy of the DTH inflammatory response from the mini-pig;
   (b) mincing the tissue biopsy in an ice cold lysing buffer to produce a minced tissue biopsy suspension;
   (c) cooling on ice the minced tissue biopsy suspension for 30 minutes;
   (d) spinning the cooled, minced tissue biopsy suspension;

(e) decanting a tissue supernatant from the spun Tissue biopsy suspension; and (f) quantitating the DTH inflammatory response of the tissue supernatant by measuring the surface antigen expressed by the infiltrating cells found in the tissue supernatant isolated from the tissue biopsy of the inflammatory response, using a capture ELISA method.

6. The method, as recited in claim 3, wherein the capture ELISA method comprises the steps of:

(a) reacting the supernatant with a first antibody, Ab(A) for a period of 12 to 16 hours;

(b) washing the reaction mixture with 0.05% Tween in PBS solution;

(c) reacting the Ab(A) linked tissue supernatant with a second antibody which is conjugated with biotin, Ab(B);

(d) washing the reaction mixture with 0.05% Tween in PBS solution;

(e) reacting the Ab(B)-Ab(A) linked tissue supernatant with a avidin-peroxidase;

(f) washing the reaction mixture with 0.05% Tween in PBS solution;

(g) reacting with substrate, o-phenylenediamine dihydrochloride;

(h) measuring the optical density of the reaction of avidin-peroxidase-Ab(B)-Ab(A) linked tissue supernatant with the substrate; and (i) calculating a cellular concentration from the optical density measured using a standard curve.

7. The method, as recited in claim 5, wherein the capture ELISA method comprises the steps of:

(a) reacting the supernatant with a first antibody, Ab(A) for a period of 12 to 16 hours;

(b) washing the reaction mixture with 0.05% Tween in PBS solution;

(c) reacting the Ab(A) linked tissue supernatant with a second antibody which is conjugated with biotin, Ab(B);

(d) washing the reaction mixture with 0.05% Tween in PBS solution;

(e) reacting the Ab(B)-Ab(A) linked tissue supernatant with a avidin-peroxidase;

(f) washing the reaction mixture with 0.05% Tween in PBS solution;

(g) reacting with substrate, o-phenylenediamine dihydrochloride;

(h) measuring optical density of the reaction of avidin-peroxidase-Ab(B)-Ab(A) linked tissue supernatant with the substrate;

(i) calculating a cellular concentration from the optical density measured using a standard curve.

8. The method, as recited in claim 4, wherein the capture ELISA method comprises:

(a) reacting the tissue supernatant with a first antibody, Ab(A) for a period of 12 to 16 hours;

(b) washing the reaction mixture with 0.05% Tween in PBS solution;

(c) reacting the Ab(A)-linked tissue supernatant with a second antibody which is conjugated with biotin, Ab(B);

(d) washing the reaction mixture with 0.05% Tween in PBS solution;

(e) reacting the Ab(B)-Ab(A)-linked tissue supernatant with a avidin-peroxidase;

(f) washing the reaction mixture with 0.05% Tween in PBS solution;

(g) reacting with substrate, o-phenylenediamine dihydrochloride;

(h) measuring optical density of the reaction of avidin-peroxidase-Ab(B)-Ab(A)-linked tissue supernatant with the substrate;

(i) calculating a cellular concentration from the optical density measured using a standard curve.

9. The method, as recited in claim 8, wherein the capture ELISA method comprises:

(a) incubating a 96-well plate treated with a first antibody Ab(A) for a period of 18 to 24 hours;

(b) washing the first antibody Ab(A) treated 96-well plate to remove the excess antibody Ab(A);

(c) blocking the plate with 3% bovine serum albumin in a phosphate buffer;

(d) reacting the tissue supernatant with the first antibody Ab(A) coated 96-well plate for a period of 12 to 16 hours;

(e) washing the reaction mixture with 0.05% Tween in PBS solution;

(f) reacting the washed 96-well plate containing the Ab(A)-linked tissue supernatant with a second antibody which is conjugated with biotin Ab(B);

(g) washing the 96-well plate containing the Ab(B)-Ab(A)-linked tissue supernatant with 0.05% Tween in PBS solution;

(h) reacting the washed 96-well plate containing the Ab(B)-Ab(A)-linked tissue supernatant with a avidin-peroxidase;

(i) washing the avidin-peroxidase treated 96-well plate containing the Ab(B)-Ab(A)-linked tissue supernatant with 0.05% Tween in PBS solution;

(j) reacting the washed avidin-peroxidase treated 96-well plate containing the Ab(B)-Ab(A)-linked tissue supernatant with substrate, o-phenylenediamine dihydrochloride;

(k) measuring optical density of the substrate-avidin-peroxidase-Ab(B)-Ab(A)-linked tissue supernatant; and (l) calculating a cellular concentration from the optical density measured using a standard curve.

10. A method for quantitating the pharmaceutical effectiveness of a test compound to inhibit or reduce the amount of cellular infiltration in a inflammatory response of a mammal comprising the steps of:

(a) solubilizing a control tissue biopsy from mammal to isolate a tissue supernatant;

(b) measuring optical density of a surface antigen expressed by the cellular infiltration found in the tissue supernatant isolated from the control tissue biopsy, using a capture ELISA method;

(c) treating the mammal with a test compound at a dose of about 8 µg/kg–30 mg/kg;

(d) solubilizing a test tissue biopsy after treatment with the test compound to isolate a tissue supernatant;

(e) quantitating the inflammatory response of the tissue supernatant by measuring optical density of a surface antigen expressed by the cellular infiltration found in the tissue supernatant isolated from the test tissue biopsy, using a capture ELISA method;

(f) calculating a cellular concentration from the measured optical density of the control and the test tissue biopsies using a standard curve; and (g) comparing the cellular infiltration concentration of the test tissue biopsy to the control tissue biopsy.

* * * * *